(12) United States Patent
Ogawa et al.

(10) Patent No.: US 6,607,791 B1
(45) Date of Patent: Aug. 19, 2003

(54) LIQUID CRYSTAL COMPOSITION

(75) Inventors: Shinji Ogawa, Saitama (JP); Masashi Osawa, Saitama (JP); Hiroyuki Ohnishi, Saitama (JP); Haruyoshi Takatsu, Tokyo (JP); Kiyofumi Takeuchi, Tokyo (JP); Shotaro Kawakami, Saitama (JP); Takeshi Kuriyama, Saitama (JP)

(73) Assignee: Dainippon Ink and Chemicals, Inc., Tokyo (JP)

( * ) Notice: Subject to any disclaimer, the term of this patent is extended or adjusted under 35 U.S.C. 154(b) by 128 days.

(21) Appl. No.: 09/696,978

(22) Filed: Oct. 27, 2000

(30) Foreign Application Priority Data

Oct. 28, 1999 (JP) ............................................. 11-306820

(51) Int. Cl.$^7$ ........................ C09K 19/30; C09K 19/52; C09K 19/34; C09K 19/20
(52) U.S. Cl. .............. 428/1.1; 252/299.01; 252/299.61; 252/299.63; 252/299.67
(58) Field of Search ........................ 252/299.63, 299.01, 252/299.61, 299.67; 428/1.1; 570/129, 144; 558/425

(56) References Cited

U.S. PATENT DOCUMENTS

| 5,458,805 A | 10/1995 | Wächtler et al. | ........ 252/299.63 |
| 5,891,360 A | 4/1999 | Wächtler et al. | ........ 252/299.63 |
| 6,284,154 B1 * | 9/2001 | Wachtler et al. | ........ 252/299.63 |

FOREIGN PATENT DOCUMENTS

DE 199 43 649 A1 6/2000

* cited by examiner

Primary Examiner—Shean C. Wu
(74) Attorney, Agent, or Firm—Armstrong, Westerman & Hattori, LLP

(57) ABSTRACT

A liquid crystal composition comprises as a first liquid crystal component a compound represented by the following general formula (I):

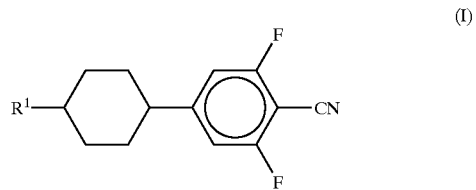

and as a second liquid crystal component a compound selected from the group consisting of compounds represented by the following general formulae (II) and (III):

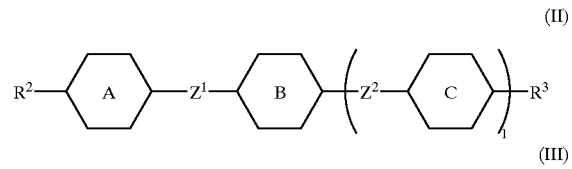

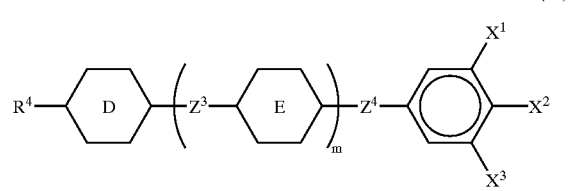

and has a nematic phase upper temperature limit of 75° C. or higher and Δn of from 0.07 to 0.18.

18 Claims, No Drawings

LIQUID CRYSTAL COMPOSITION

FIELD OF THE INVENTION

The present invention relates to a nematic liquid crystal composition useful as an electro-optical liquid crystal display material and a liquid crystal display device comprising such a nematic liquid crystal composition.

BACKGROUND OF THE INVENTION

Since its appearance as a display for desk electronic calculator, a liquid crystal display device (LCD) has met the demand for display capacity, i.e., from TN-LCD (twisted-nematic liquid crystal display device) to STN-LCD, with the progress of development of computer. STN-LCD was developed Scheffer et al. [SID '85 Digest, page 120 (1985)] or Kinugawa et a. [SID '86 Digest, page 122 (1986)] and has been widely spread for display for high data processors such as word processor and personal computer. An active addressing drive system has been recently proposed for the purpose of improving the response in STN-LCD (see Proc. 12th International Display Research Conference p. 503 (1992)). Good display properties over a wider temperature range have been required for portable terminal display (Personal Digital Assistance). Such a liquid crystal material is required to have a low viscosity and a low constant driving voltage over a wide temperature range. Such a liquid crystal material is also required to have no fluctuations in driving voltage within a frequency range corresponding to various time-division multiplexes. However, the background art liquid crystal material leaves something to be desired in response (switching time) and contrast developed when assembled into display device. Thus, new liquid crystal compounds or liquid crystal compositions are still proposed.

As mentioned above, one of the important problems TN-LCD and STN-LCD are facing is enhancement of contrast. With the rapid expansion of its use, LCD has been used more and more for indoor use but also for outdoor use under severe temperature conditions as in the case of portable terminal display for computer and display for on-board meter and outdoor measuring instrument. Thus, problem of deterioration of display quality have arisen due to the reduction of display contrast caused by the change of temperature in the atmosphere when LCD is installed and the reduction of response at low temperatures. LCD has also been required to have a high reliability in outdoor use.

The reduction of LCD display quality due to the change of ambient temperature is attributed to various causes. As these causes there can be considered the change of elastic constant and dielectric constant of nematic liquid crystal with temperature and the change of threshold voltage Vth with temperature due to the change of inherent pitch of a chiral material with temperature. Accordingly, a proposal for the improvement of temperature dependence of threshold voltage by the control of the inherent pitch of a chiral material has been already known (JP-A-55-38869 (The term "JP-A" as used herein means an "unexamined published Japanese patent application")). Problems have arisen that different combination of a matrix liquid crystal and a chiral material have different effects and the increase of the content of a chiral material has an adverse effect on the display properties such as response.

However, the change of mobility of an ionic material contained in the liquid crystal with temperature causes an increase of current flow. Accordingly, no countermeasures have been known against phenomena caused by the consumption of the effective voltage applied to the liquid crystal by ions resulting in the deterioration of contrast and reliability. From this standpoint of view, it is necessary that the amount of a compound having ester bond which has heretofore been widely used be reduced. However, the resulting rise of threshold voltage has caused a problem.

As a material which is free of ester bond but reduces the threshold voltage of liquid crystal there has already been known a material having 2,6-difluorobenzonitrile skeleton. However, the use of such a material having a large dielectric anisotropy has an adverse effect on response. Therefore, such a material must be used in a limited amount that often makes it impossible to provide a sufficient effect. As a material for improving response there has been known a compound having an alkenyl group incorporated in its side chain (JP-A-4-296387). However, 1-alkenyl group, which has a great effect, cannot be used from the standpoint of stability unless it is connected to cyclohexane ring. Further, 3-alkenyl group and alkyl-substituted 1-alkenyl group provide a great elastic constant ratio and thus have insufficient effect of lowering threshold voltage.

SUMMARY OF THE INVENTION

An object of the invention is to provide a liquid crystal composition which allows inhibited current flow and exhibits a high reliability without deteriorating various properties of liquid crystal such as threshold voltage and response.

A further object of the invention is to attain desired display properties such as high stabilized contrast (steepness) over a wider temperature range by improving the temperature dependence of threshold voltage.

A still further object of the invention is to provide a 2,6-difluorobenzonitrile derivative compound useful as a constituent material of such a liquid crystal composition. The use of such a liquid crystal composition for liquid crystal display device provides an effect of improving the properties of display, e.g., on 1/32 to 1/400 duty, preferably 1/80 to 1/250 duty, making it possible to provide a liquid crystal display device (STN-LCD) having enhanced contrast against increase of data or color display.

In order to solve the foregoing problems, the inventors made studies of liquid crystal compositions comprising various liquid crystal compounds. As a result, the following liquid crystal compositions were found.

Invention 1:

A liquid crystal composition comprising as a first liquid crystal component at least one compound selected from the group consisting of compounds represented by the following general formula (I):

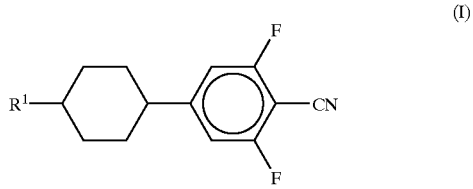

wherein $R^1$ represents a $C_{2-16}$ alkenyl group or $C_{3-16}$ alkenyloxy group
and as a second liquid crystal component at least one compound selected from the group consisting of compounds represented by the following general formulae (II) and (III):

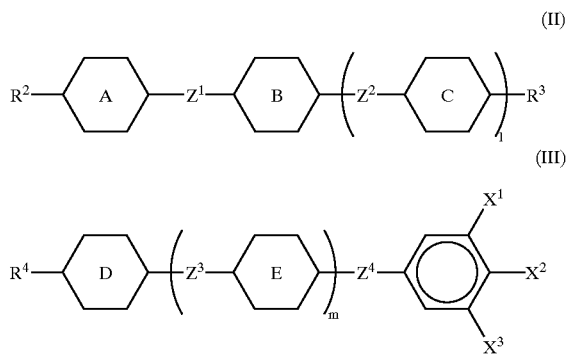

(II)

(III)

wherein $R^2$, $R^3$ and $R^4$ each independently represents a $C_{1\text{-}16}$ alkyl or alkoxyl group which may be substituted by a fluorine atom, a $C_{2\text{-}16}$ alkenyl group which may be substituted by a fluorine atom, a $C_{3\text{-}16}$ alkenyloxy group which may be substituted by a fluorine atom or a $C_{1\text{-}10}$ alkoxyl group-substituted $C_{1\text{-}12}$ alkyl group which may be substituted by a fluorine atom; the rings A, B, C, D and E each independently represents a 1,4-phenylene group, 2-methyl-1,4-phenylene group, 3-methyl-1,4-phenylene group, naphthalene-2,6-diyl group, phenanthrene-2,7-diyl group, fluorene-2,7-diyl group, trans-1,4-cyclohexylene group, 1,2,3,4-tetrahydronaphthalene-2,6-diyl group, decahydronaphthalene-2,6-diyl group, trans-1,3-dioxane-2,5-diyl group, pyridine-2,5-diyl group, pyrimidine-2,5-diyl group, pyrazine-2,5-diyl group or pyridazine-2,5-diyl group, each of which may be substituted by a fluorine atom; l and m each independently representss 0, 1 or 2; $Z^1$, $Z^2$, $Z^3$ and $Z^4$ each independently represents a single bond, —$CH_2CH_2$—, —$(CH_2)_4$—, —$OCH_2$—, —$CH_2O$—, —CH=CH—, —CH=N—N=CH— or —C≡C—; $X^2$ represents a cyano group, a fluorine atom, a chlorine atom, a trifluoromethoxy group, a trifluoromethyl group, a difluoromethoxy group, a hydrogen atom, a 3,3,3-trifluoroethoxy group, R' or —OR' in which R' represents a $C_{1\text{-}12}$ straight-chain alkyl group or a $C_{2\text{-}12}$ straight-chain alkenyl group; and $X^1$ and $X^3$ each independently representss a hydrogen atom, a fluorine atom or a chlorine atom, with the proviso that when $R^4$ is an alkenyl or alkenyloxy group, $X^2$ is a cyano group, the ring D is a trans-1,4-cyclohexylene group, m is 0, and $Z^4$ is a single bond, $X^1$ and $X^3$ are not a fluorine atom at the same time and said composition having a nematic phase upper temperature limit of 75° C. or higher and a birefringence (Δn) of from 0.07 to 0.24

Invention 2:

The liquid crystal composition according to Invention 1, wherein the content of the at least one compound of the general formula (I) in the composition is from 5 to 40% by weight and the content of the at least one compound selected from the group consisting of compounds represented by the formulae (II) and (III) in the composition is from 5 to 95% by weight.

Invention 3:

The liquid crystal composition according to Invention 1 or 2, wherein as the compound of the general formula (II) there is incorporated at least one compound selected from the group consisting of compounds of the following general formula (II-a):

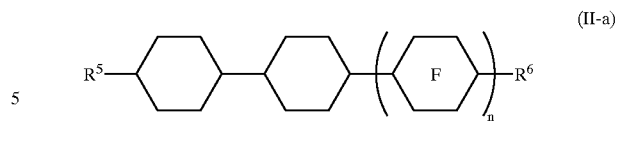

wherein $R^5$ and $R^6$ have the same meaning as $R^2$ and $R^3$, respectively; the ring F represents a 1,4-phenylene group or trans-1,4-cyclohexylene group; and n represents 0 or 1.

Invention 4:

The liquid crystal composition according to Invention 3, wherein the content of the at least one compound of the general formula (I) in the composition is from 5 to 40% by weight and the content of the at least one compound of the general formula (II-a) in the composition is from 5 to 95% by weight.

Invention 5:

The liquid crystal composition according to any one of Inventions 1 to 4, wherein as the compound of the general formula (III) there is incorporated at least one compound selected from the group consisting of compounds of the following general formula (III-a):

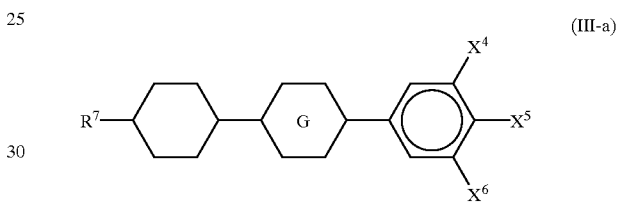

wherein $R^7$ represents a $C_{1\text{-}8}$ alkyl group or a $C_{2\text{-}8}$ alkenyl group; the ring G represents a 1,4-phenylene group or a trans-1,4-cyclohexylene groupl $X^5$ represents a cyano group, a fluorine atom, a trifluoromethoxy group or a difluoromethoxy group; and $X^4$ and $X^6$ each independently represents a hydrogen atom or a fluorine atom.

Invention 6:

The liquid crystal composition according to Invention 5, wherein the content of the at least one compound of the general formula (I) in the composition is from 5 to 40% by weight and the content of the at least one compound of the general formula (III-a) in the composition is from 5 to 95% by weight.

Invention 7:

The liquid crystal composition according to any one of Inventions 1 to 6, wherein said composition comprises as the first liquid crystal component at least one compound of the general formula (I) in an amount of from 5 to 40% by weight, and as the second liquid crystal component at least one compound selected from the group consisting of compounds represented by the following general formula (II-b) in an amount of from 5 to 40% by weight:

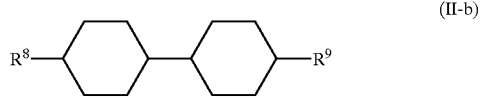

wherein $R^8$ and $R^9$ each independently representss a $C_{1\text{-}8}$ alkyl group or a $C_{2\text{-}8}$ alkenyl group and at least one compound selected from the group consisting of compounds represented by the following general formula (II-c) in an amount of from 5 to 60% by weight:

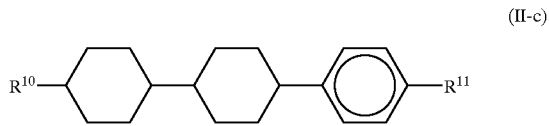

wherein $R^{10}$ and $R^{11}$ each independently represents a $C_{1-8}$ alkyl group or a $C_{2-8}$ alkenyl group.

Invention 8:

The liquid crystal composition according to any one of Inventions 1 to 7, wherein said composition comprises as the first liquid crystal component at least one compound of the general formula (I) in an amount of from 5 to 40% by weight and as the second liquid crystal component at least one compound selected from the group consisting of compounds represented by the following general formula (III-a) in an amount of from 5 to 40% by weight:

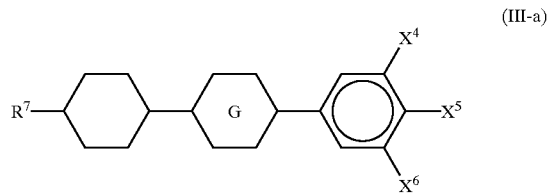

wherein $R^7$ represents a $C_{1-8}$ alkyl group or a $C_{2-8}$ alkenyl group; the ring G represents a 1,4-phenylene group or a trans-1,4-cyclohexylene group; $X^5$ represents a cyano group, a fluorine atom, a trifluoromethoxy group or a difluoromethoxy group; and $X^4$ and $X^6$ each independently representss a hydrogen atom or a fluorine atom, and at least one compound selected from the group consisting of compounds represented by the following general formulae (II-b) and (II-c) in an amount of from 5 to 60% by weight:

wherein $R^8$ and $R^9$ each independently representss a $C_{1-8}$ alkyl group or a $C_{2-8}$ alkenyl group,

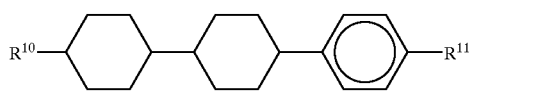

wherein $R^{10}$ and $R^{11}$ each independently represents a $C_{1-8}$ alkyl group or a $C_{2-8}$ alkenyl group.

Invention 9:

The liquid crystal composition according to any one of Inventions 1 to 8, wherein said composition comprises as the first liquid crystal component at least one compound of the general formula (I) in an amount of from 5 to 40% by weight and as the second liquid crystal component at least one compound selected from the group consisting of compounds represented by the following general formula (III-a) in an amount of from 5 to 40% by weight:

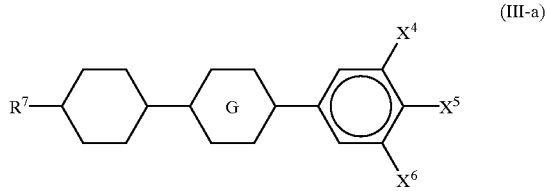

wherein $R^7$ represents a $C_{1-8}$ alkyl group or a $C_{2-8}$ alkenyl group; the ring G represents a 1,4-phenylene group or a trans-1,4-cyclohexylene groupl $X^5$ represents a cyano group, a fluorine atom, a trifluoromethoxy group or a difluoromethoxy group; and $X^4$ and $X^6$ each independently representss a hydrogen atom or a fluorine atom, at least one compound selected from the group consisting of compounds represented by the following general formula (II-b) in an amount of from 5 to 40% by weight:

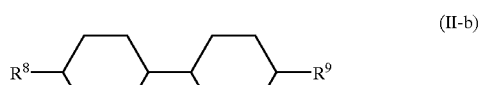

wherein $R^8$ and $R^9$ each independently representss a $C_{1-8}$ alkyl group or a $C_{2-8}$ alkenyl group, and at least one compound selected from the group consisting of compounds represented by the following general formula (II-c) in an amount of from 5 to 40% by weight:

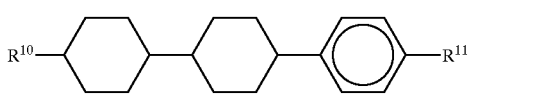

wherein $R^{10}$ and $R^{11}$ each independently representss a $C_{1-8}$ alkyl group or a $C_{2-8}$ alkenyl group.

Invention 10:

The liquid crystal composition according to any one of Inventions 1 to 9, wherein as the compound of the general formula (III) there is incorporated at least one compound selected from the group consisting of compounds represented by the following general formula (III-b):

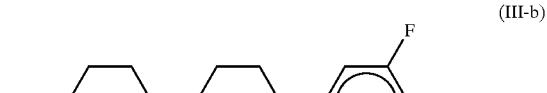

wherein $R^{12}$ represents a $C_{1-16}$ alkyl group or a $C_{2-8}$ alkenyl group in an amount of from 5 to 40% by weight.

Invention 11:

The liquid crystal composition according to any one of Inventions 1 to 9, wherein as the compound of the general formula (III) there is incorporated at least one compound selected from the group consisting of compounds represented by the following general formula (III-c):

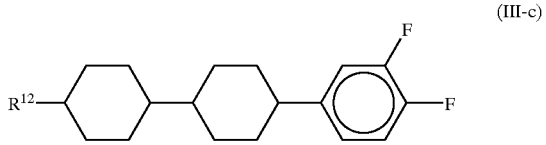

(III-c)

wherein $R^{12}$ represents a $C_{1-16}$ alkyl group or a $C_{2-8}$ alkenyl group in an amount of from 5 to 40% by weight.

Invention 12:

A compound represented by the following general formula (Ia):

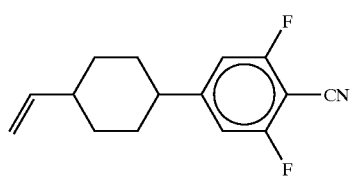

(Ia)

Invention 13:

The liquid crystal composition according to any one of Inventions 1 to 11, wherein as said first component there is incorporated a compound represented by the general formula (Ia).

Invention 14:

The nematic liquid crystal composition according to any one of Inventions 1 to 11 and 13, which satisfies at least one of the following requirements:

(i) $0.11 \leq \Delta n \leq 0.195$;

(ii) $4 \leq \Delta \epsilon \leq 60$;

(iii) $1.1 \leq K33/K11 \leq 3$;

(iv) $10 \text{ m.Pas} \leq \eta 80 \text{ m.Pas}$; and (v) $75° \text{ C.} \leq T_{N-I} \leq 130° \text{ C.}$ wherein the measurement for the requirements (i) to (iv) are made at 20° C., $\Delta n$ represents a birefringence, $\Delta \eta$ represents a dielectric anistropy, K33/K11 represents an elastic constant ratio, K33 represents a bend elastic constant, K11 represents a splay elastic constant, $\eta$ represents a viscosity and $T_{N-I}$ represents nematic phase-isotropic liquid phase transition temperature.

Invention 15:

A liquid crystal display device comprising the liquid crystal composition according to any one of Inventions 1 to 11, 13 and 14.

Invention 16:

A super-twisted nematic (STN) liquid crystal display device comprising the liquid crystal composition according to any one of Inventions 1 to 11, 13 and 14, having a twist angle of from 220° to 270° and satisfying at least one of the following requirements (i) to (iii) when the driving temperature falls within the range of from −20° C. to 60° C.

(i) $\Delta V/\Delta T$ (temperature dependence of Vth) $\leq 7$ mV/° C;

(ii) Steepness $\gamma$ (ratio of saturation voltage to threshold voltage (Vth))$\leq 1.15$; and (iii) Ratio of minimum to maximum of steepness $\gamma$ in the foregoing temperature range $\leq 3\%$.

DETAILED DESCRIPTION OF THE INVENTION

An embodiment of implication of the present invention will be described hereinafter. In Invention 1, as the first liquid crystal component there are incorporated one or more compounds selected from the group consisting of compounds represented by the general formula (I), preferably there are incorporated one or two compounds represented by the general formula (I). In the general formula (I), $R^1$ represents a $C_{2-16}$ alkenyl group or a $C_{3-16}$ alkenyloxy group, preferably a $C_{2-16}$ alkenyl group, more preferably a $C_{2-8}$ alkenyl group, even more preferably any one of the following structures (a) to (e);

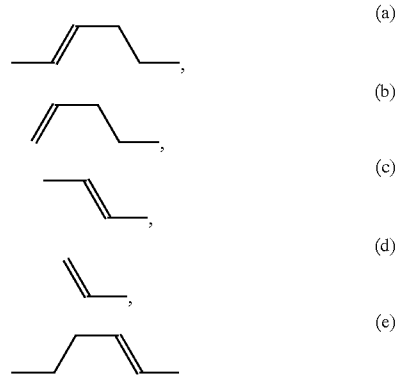

(These structures are each connected to a ring at the right end thereof).

Particularly preferred among these structures is (d). The liquid crystal composition of the invention further comprises as the second liquid crystal component one or more, preferably 3 or more, more preferably from 3 to 20, particularly from 5 to 15 compounds selected from the group consisting of compounds represented by the general formulae (II) and (III). Even more preferably, there are incorporated at least two compounds of the general formula (II).

This liquid crystal composition is characterized by the nematic phase upper temperature limit of 75° C. or higher, preferably 80° C. or higher, particularly preferably 85° C. or higher. The birefringence (optical anisotropy) $\Delta n$ is from 0.07 to 0.24, preferably from 0.08 to 0.22. $R^2$, $R^3$ and $R^4$ each independently represents a $C_{1-16}$ alkyl or alkoxyl group which may be substituted by a fluorine atom, a $C_{2-16}$ alkenyl group which may be substituted by a fluorine atom, a $C_{3-16}$ alkenyloxy group which may be substituted by a fluorine atom or a $C_{1-10}$ alkoxyl group-substituted $C_{1-12}$ alkyl group which may be substituted by a fluorine atom, preferably a $C_{1-16}$ alkyl group or a $C_{2-16}$ alkenyl group, more preferably a $C_{1-8}$ alkyl group or a $C_{2-8}$ alkenyl group, particularly preferably a $C_{1-5}$ alkyl group or an alkenyl group having the above structure (a), (b), (c), (d) or (e). The rings A, B, C, D and E each independently represents a 1,4-phenylene group, 2-methyl-1,4-phenylene group, 3-methyl-1,4-phenylene group, naphthalene-2,6-diyl group, phenanthrene-2,7-diyl group, fluorene-2,7-diyl group, trans-1,4-cyclohexylene group, 1,2,3,4-tetrahydronaphthalene-2,6-diyl group, decahydronaphthalene-2,6-diyl group, trans-1,3-dioxane-2,5-diyl group, a pyridine-2,5-diyl group, pyrimidine-2,5-diyl group, pyrazine-2,5-diyl group or pyridazine-2,5-diyl group, each of which may be substituted by a fluorine atom, preferably a 1,4-phenylene group or a trans-1,4-cyclohexylene group. Preferred among the groups represented by the rings A, B, D and E is a trans-1,4-cyclohexyl group. Preferred among the groups represented by the ring C is a 1,4-phenylene group. The suffixes l and m each independently represents 0, 1 or 2, preferably 0 or 1. $Z^1$, $Z^2$, $Z^3$ and $Z^4$ each independently represents a single bond, —CH$_2$CH$_2$—, —(CH$_2$)$_4$—, —OCH$_2$—, —CH$_2$O—, —CH=CH—, —CH=N—N=CH— or —C≡C—. Preferred among the groups represented by $Z^1$ and $Z^2$ is a single bond or —$CH_2CH_2$—, more preferably a singlebond. Preferred among the groups represented by $Z^3$ and $Z^4$ is a single bond or —C=C—, more preferably a single bond. $X^2$ represents a cyano group, a fluorine atom, a chlorine atom, a trifluoromethoxy group, a trifluoromethyl group, a difluoromethoxy group, a hydrogen atom, a 3,3,3-trifluoroethoxy group, R' or —OR' in which R' represents a $C_{1-12}$ straight-chain alkyl group or a $C_{2-12}$ straight-chain alkenyl group, preferably a cyano group, a fluorine atom, a trifluoromethoxy group or a difluoromethoxy group, more preferably a fluorine atom, a trifluoromethoxy group or a difluoromethoxy group, particularly preferably a fluorine atom. $X^1$ and $X^3$ each represents a hydrogen atom, a fluorine atom or a chlorine atom, preferably a hydrogen atom or a fluorine atom, particularly preferably a fluorine atom.

In Invention 2, the content of the compound of the general formula (I) is from 5 to 40% by weight, preferably from 5 to 25% by weight, particularly preferably from 5 to 20% by weight. The content of the compound represented by the general formula (II) or (III) is from 5% to 95% by weight, preferably from 15% to 85% by weight, particularly preferably from 25% to 85% by weight.

In Invention 4, there are incorporated one or more compounds of the general formula (I) in an amount of from 5% to 40% by weight and one or more compounds of the general formula (II-a) in an amount of from 5% to 95% by weight. Preferably, there are incorporated one or two compounds of the general formula (I) in an amount of from 5% to 25% by weight, particularly preferably from 5% to 20% by weight, and two or more compounds of the general formula (II-a) in an amount of from 5% to 95% by weight, more preferably from 15% to 85% by weight, particularly preferably from 25% to 85% by weight.

In Invention 6, there are incorporated one or more compounds of the general formula (I) in an amount of from 5% to 40% by weight and one or more compounds of the general formula (III-a) as the second liquid crystal component in an amount of from 5% to 95% by weight. Preferably, there are incorporated one or two compounds of the general formula (I) in an amount of from 5% to 25% by weight, particularly preferably from 5% to 15% by weight, and two or more compounds of the general formula (III-a) in an amount of from 5% to 95% by weight, more preferably from 15% to 855 by weight, particularly preferably from 25% to 85% by weight.

In Invention 7, there are incorporated one or more compounds of the general formula (I) in an amount of from 5% to 40% by weight and one or more compounds selected from the group consisting of compounds represented by the general formula (II-b) in an amount of from 5% to 40% by weight, preferably from 5% to 25% by weight. There are further incorporated one or more compounds selected from the group consisting of compounds represented by the general formula (II-c) in an amount of from 5% to 60% by weight, preferably from 5% to 50% by weight, more preferably from 5% to 40% by weight. $R^8$, $R^9$, $R^{10}$ and $R^{11}$ each independently represents a $C_{1-8}$ alkyl group or a $C_{2-8}$ alkenyl group. Particularly preferred are a $C_{1-5}$ alkyl group and an alkenyl group having the above structure (a), (b), (c), (d) or (e).

In Invention 8, there are incorporated one or more compounds of the general formula (I) of Invention 1 in an amount of from 5% to 40% by weight, one or more compounds of the general formula (III-a) in an amount of from 5% to 40% by weight, and one or more compounds of the general formula (II-b) or (II-c) in an amount of from 5% to 60% by weight. Preferably, there are incorporated one or two compounds of the general formula (I) in an amount of from 5% to 20% by weight. The content of the compounds of the general formula (III-a) is preferably from 5% to 35% by weight, more preferably from 5% to 25% by weight. The content of the compounds of the general formula (II-b) or (II-c) is preferably from 5% to 55% by weight, more preferably from 5% to 45% by weight.

In Invention 9, there are incorporated one or more compounds of the general formula (I) of Invention 1 in an amount of from 5% to 40% by weight, one or more compounds of the general formula (III-a) in an amount of from 5% to 40% by weight, and one or more compounds of the general formula (II-b) or (II-c) in an amount of from 5% to 40% by weight. Preferably, there are incorporated one or two compounds of the general formula (I) in an amount of from 5% to 20% by weight, one or more of each of the compounds of the general formulae (II-b) and (II-c) in an amount of from 5% to 20% by weight, and two or more compounds of the general formula (III-a) in an amount of from 5% to 25% by weight.

In Invention 10, there are incorporated as compounds of the general formula (III) of Invention 1 or (III-a) one or more compounds selected from the group consisting of compounds represented by the general formula (III-b) in an amount of from 5% to 40% by weight. Preferably, there are incorporated 1 to 10 compounds of the general formula (III-b) in an amount of from 5% to 35% by weight. More preferably, there are incorporated 1 to 5 compounds of the general formula (III-b) in an amount of from 5% to 30% by weight. In the general formula (III-b), $R^{12}$ represents a $C_{1-8}$ alkyl group or a $C_{2-8}$ alkenyl group. Particularly preferred are a $C_{1-5}$ alkyl group and an alkenyl group having the above structure (a), (b), (c), (d) or (e).

In Invention 11, there are incorporated as compounds of the general formula (III) of Invention 1 or (III-a) one or more compounds selected from the group consisting of compounds represented by the general formula (III-c) in an amount of from 5% to 40% by weight. Preferably, there are incorporated 1 to 10 compounds of the general formula (III-c) in an amount of from 5% to 35% by weight. More preferably, there are incorporated 1 to 5 compounds of the general formula (III-c) in an amount of from 5% to 30% by weight. In the general formula (III-c), $R^{12}$ represents a $C_{1-8}$ alkyl group or a $C_{2-8}$ alkenyl group. Particularly preferred are a $C_{1-5}$ alkyl group and an alkenyl group having the above structure (a), (b), (c), (d) or (e).

In Invention 13, there is a compound of the general formula (I-a) defined in Invention 12 in an amount of preferably from 5 to 40% by weight, more preferably from 5 to 20% by weight.

In a preferred embodiment the liquid crystal composition described above satisfies one or more of the following requirements (i) or (v). The measurement for the requirements (i) to (iv) are made at 20° C.

(i) The birefringence $\Delta n$ . . . of the liquid crystal composition is preferably from 0.11 to 0.195, more preferably from 0.13 to 0.18 for the design of the thickness of STN-LCD cell.

(ii) The dielectric anisotropy $\Delta \epsilon$ of the liquid crystal composition is normally preferably from 4 to 60, more preferably from 4 to 13 when the threshold voltage falls within the range of from 1.8 V to 2.9 V, from 5 to 18 when the threshold voltage falls within the range of from 1.5 V to 1.9 V, 8 to 24 when the threshold voltage falls within the range of from 1.2 V to 1.6 V, 12 to 45 when the threshold voltage falls within the range of from 0.8 V to 1.3 V.

(iii) The elastic constant ratio K33/K11 can be properly designed to be from 1.1 to 3, more preferably from 1.3 to 2.5 for even more desirable steepness and response. A liquid crystal composition comprising as an essential component a compound of the general formula (I), particularly a compound of the general formula (Ia), exhibited a steepness high enough to provide a high contrast even when the threshold voltage is as relatively low as from 0.8 V to 1.8 V. This effect is developed by the selective incorporation of essential components as described in detail above. This effect is developed also because the elastic constant ratio K33/K11 can be properly adjusted to be from 1.3 to 2.5.

(iv) The viscosity of the liquid crystal composition is from 10 mPa.s to 80 m.Pa.s. The viscosity of the liquid crystal composition can be designed depending on the desired threshold voltage. The viscosity of the liquid crystal composition is preferably from 10 mPa.s to 45 mPa.s. The liquid crystal composition of the invention can maintain desired response due to the incorporation of a compound of the general formula (I), particularly the general formula (Ia), as a main component even if it has a viscosity of from 25 mPa.s to 30 mPa.s or more.

(v) The nematic phase-isotropic liquid phase transition temperature $T_{N-I}$ of the liquid crystal composition can be designed to be from 75° C. to 130° C., preferably from 80° C. to 110° c. for portable use or outdoor use.

It goes without saying that one or more of these requirements (i) or (v) described in detail above are preferably satisfied.

In Invention 16, the super-twisted nematic (STN) liquid crystal display device is preferably in the following embodiment. The twist angle of the super-twisted nematic liquid crystal display device can be predetermined to be from 180° to 360°, preferably from 220° to 270°. The liquid crystal display device of the invention preferably satisfies at least one of the following requirements when the driving temperature falls within the range of −20° C. to 60° C.

(i) The temperature dependence of Vth ΔV/ΔT is preferably 7 mV or less, more preferably 5 mV or less when the threshold voltage falls within the range of from 0.8 V to 1.8 V, 4 mV or less when the threshold voltage falls within the range of from 0.8 V to 1.6 V.

(ii) The steepness γ (ration of saturation voltage Vsat to threshold voltage Vth) is preferably 1.15 or less, more preferably 1.08 or less when the threshold voltage falls within the range of from 0.8 V to 1.6 V, 1.07 or less when the threshold voltage falls within the range of from 1.0 V to 1.8 V, 1.06 or less when the threshold voltage falls within the range of from 1.2 V to 2.5 V.

(iii) The ratio of maximum to minimum of steepness γ at a temperature range of from −20° C. to 60° C. can be predetermined to be 3% or less, preferably 2% or less.

It goes without saying that one or more of these requirements (i) to (iii) descried in detail above are preferably satisfied.

The liquid crystal display device described above is STN-LCD which shows little or no increase of current flow, reduced response at low temperatures and enhanced contrast against increase of data or color display during 1/60 to 1/400 duty, preferably 1/100 to 1/250 duty display.

The foregoing nematic liquid crystal composition is useful for TN-LCD or STN-LCD, particularly STN-LCD. The foregoing nematic liquid crystal composition can be used also for transmission or reflection type liquid crystal display device. The liquid crystal composition of the invention may comprise an ordinary nematic liquid crystal compound, smectic liquid crystal compound, cholesteric liquid crystal compound or the like incorporated therein besides the foregoing compounds.

EXAMPLES

The present invention will be further described in the following examples, but the present invention should not be construed as being limited thereto. The term "%" as used for composition in the following examples and comparative examples is meant to indicate "% by weight".

The properties measured in the following examples are as follows:

$T_{N-I}$: Nematic phase-isotropic phase transition temperature (° C.)

T→N: Solid phase or smectic phase-nematic phase transition temperature (° C.)

Vth: Threshold voltage (V) in the form of TN-LCD cell having a thickness of 6 μm Δε: Dielectric anisotropy Δn: Birefringence ΔV: Vth (60° C.)–Vth(−20° C.) (mV)

ΔT: 60−(−20) (° C.)

ΔV/ΔT: |ΔV|/ΔT (mV/° C.)

η: Viscosity (mPa.s) at 20° C.

Ir: Current (μA/cm$^2$) flowing through a composition comprising a 240° twisted STN-LCD having a liquid crystal composition vacuum-injected therein which has been heated to 80° C. for 100 hours.

CR: Contrast shown when a composition comprising a 240° twisted STN-LCD having a liquid crystal composition vacuum-injected therein is driven with a 1/16 bias driving waveform on 1/200 duty The STN-LCD display device was prepared in the following manner. In some details, to a nematic liquid crystal composition was added a Type S-811 chiral material (produced by Merck Japan Ltd.) to prepare a mixed liquid crystal. The mixed liquid crystal was then injected into an STN-LCD display cell having a twist angle of 240° comprising opposing planar transparent electrodes having an alignment film of Sanever 150 (produced by Nissan Chemical Industries, Ltd.) formed thereon (film forming was accomplished by rubbing). The addition of the chiral material was effected such that the inherent spiral pitch P of the mixed liquid crystal composition and the thickness d of the display cell thus attained satisfy the following requirements:

Δn.d=0.85; and d/P=0.50

The compounds used are represented by the following abbreviations:

| Terminal n (figure) | $C_nH2_{n+1}$— |
|---|---|
| C | Trans-1,4-cyclohexylene group |
| C/ | 1,4-Cyclohexenediyl group |
| P | 1,4-Phenylene group |
| Pm | Pyrimidine-2,5-diyl group |
| E | —COO— |
| e | —OCO— |
| A | —CH$_2$CH$_2$— |
| t | —C≡C— |
| —Z— | —CH=N—N=CH— |
| CN | —C≡N |
| On | —OC$_n$H$_{2n+1}$ |
| F | —F |
| f | F atom connected to terminal group in the ortho position |
| ndm- | $C_2H_{2n+1}$—C≡C—(CH$_2$)$_{n-1}$— |
| —O(dm)n | —O(CH$_2$)$_m$-2-C≡C—C$_n$H$_{2n+1}$ |

Example 1 and Comparative Example 1
Nematic liquid crystal composition No. 1
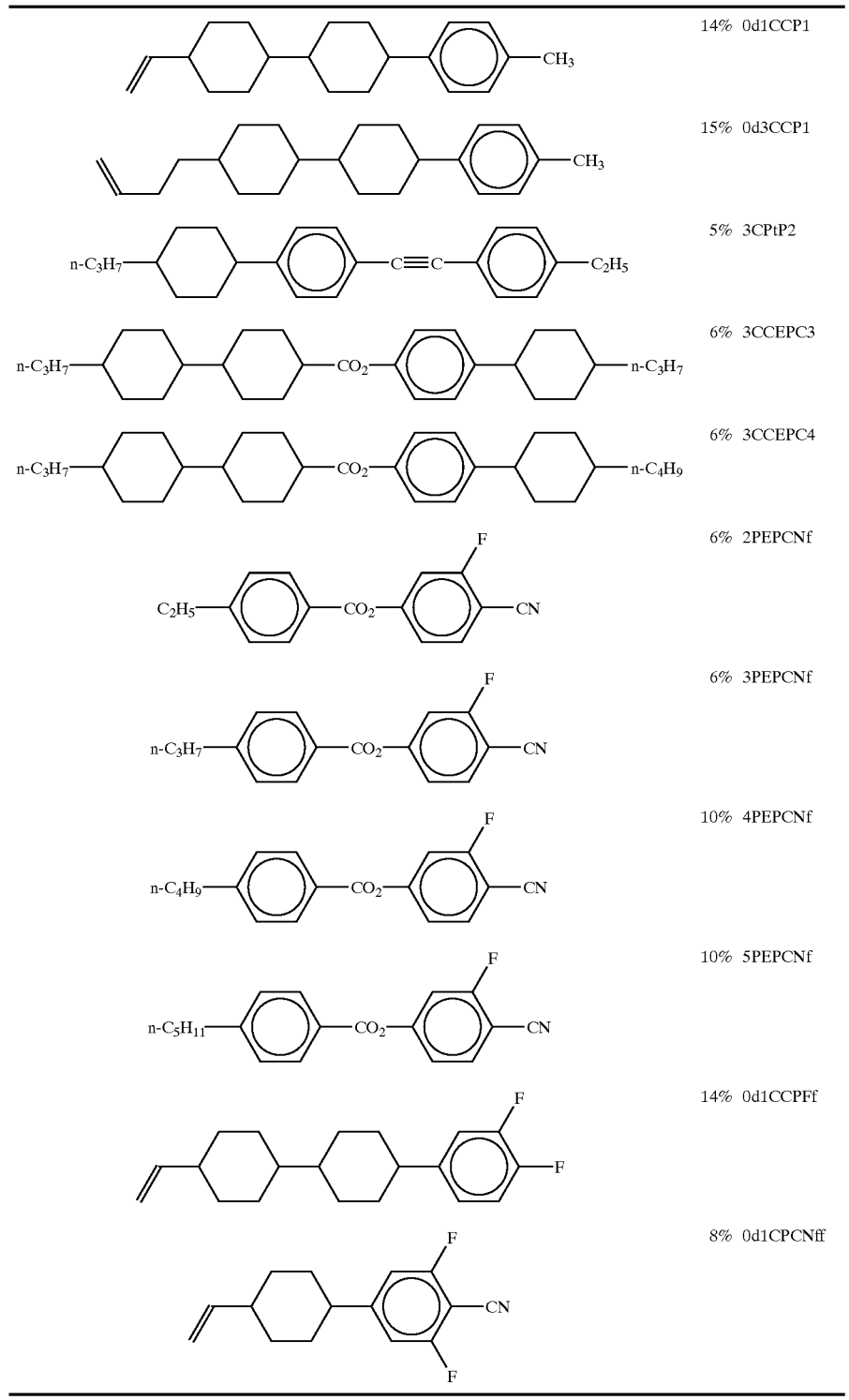

The foregoing nematic liquid crystal compositions were prepared, and then measured for various properties. The results are set forth in Table 1 together with those of Comparative Example 1.

TABLE 1

Example 1 and Comparative Example 1

| | Example 1 (No. 1) | | Comparative Example 1 | |
|---|---|---|---|---|
| Composition | 0d1CCP1 | 14% | 0d1CCP1 | 14% |
| | 0d3CCP1 | 15% | 0d3CCP1 | 15% |
| | 3CPtP2 | 5% | 3CPtP2 | 5% |
| | 3CCEPC3 | 6% | 3CCEPC3 | 6% |
| | 3CCEPC4 | 6% | 3CCEPC4 | 6% |
| | 2PEPCNf | 6% | 2PEPCNf | 6% |
| | 3PEPCNf | 6% | 3PEPCNf | 6% |
| | 4PEPCNf | 10% | 4PEPCNf | 10% |
| | 5PEPCNf | 10% | 5PEPCNf | 10% |
| | 0d1CCPFf | 14% | 0d1CCPFf | 14% |
| | 0d1CPCNff | 8% | 5PEPCNff | 8% |
| $T_{N-I}$ (° C.) | 99.6 | | 99.9 | |
| T → N (° C.) | −70 | | −70 | |
| Vth (V) | 1.03 | | 0.95 | |
| $\Delta\epsilon$ | 15.2 | | 15.79 | |
| $\Delta n$ | 0.130 | | 0.134 | |
| Ir ($\mu A/cm^2$) | 0.10 | | 0.25 | |
| CR | 5:1 | | 3:1 | |

As can be seen in Table 1 above, the liquid crystal composition of Example 1 shows a drastically inhibited current and improved contrast as compared with the liquid crystal composition of Comparative Example 1.

STN-LCD thus prepared was then used to prepare a liquid crystal display device having excellent display properties.

Example 2

A nematic liquid crystal composition No. 2 was prepared (Example 2), and then measured for various properties. The data of properties thus measured are set forth in Table 2 below together with those of a comparative composition (Comparative Example 2).

TABLE 2

Example 2 and Comparative Example 2

| | Example 2 (No. 2) | | Comparative Example 2 | |
|---|---|---|---|---|
| Composition | 0d1CC5 | 8% | 0d1CC5 | 8% |
| | 3PtP2 | 2% | 3PtP2 | 2% |
| | 0d1CCP1 | 12% | 0d1CCP1 | 12% |
| | 0d3CCP1 | 13% | 0d3CCP1 | 13% |
| | 3CCPO(d3)1 | 4% | 3CCPO(d3)1 | 4% |
| | 3CCP(d3)0 | 3% | 3CCP(d3)0 | 3% |
| | 3CPtP2 | 4% | 3CPtP2 | 4% |
| | 3CEPtP1 | 5% | 3CEPtP1 | 5% |
| | 2PEPCNf | 5% | 2PEPCNf | 5% |
| | 3PEPCNf | 5% | 3PEPCNf | 5% |
| | 4PEPCNf | 10% | 4PEPCNf | 10% |
| | 0d1CPCN | 7% | 0d1CPCN | 7% |
| | 1d1CPCN | 7% | 1d1CPCN | 7% |
| | 0d1CPCNff | 15% | 5PEPCNff | 15% |
| $T_{N-I}$ (° C.) | 90.5 | | 92.2 | |
| T → N (°C.) | −50 | | −33 | |
| Vth (V) | 1.25 | | 1.17 | |
| $\Delta\epsilon$ | 11.7 | | 14.9 | |
| $\Delta n$ | 0.134 | | 0.141 | |
| Ir ($\mu A/cm^2$) | 0.15 | | 0.32 | |
| CR | 6:1 | | 3:1 | |

As can be seen in Table 2, the liquid crystal composition of Example 3 shows a drastically inhibited current and improved contrast as compared with the liquid crystal composition of Comparative Example 2.

STN-LCD thus prepared was then used to prepare a liquid crystal display device having excellent display properties.

Example 3

Synthesis of compound of the general formula (Ia)

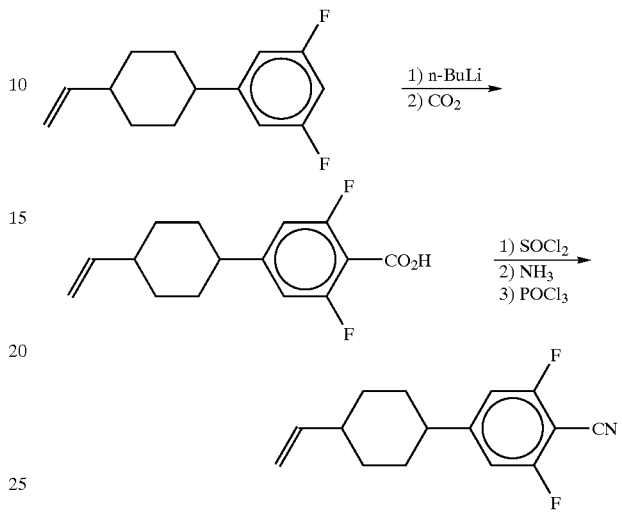

(a) Synthesis of 2,6-difluoro-4-(trans-4-vinylcyclohexyl) benzoic acid 25 g of 1,3-difluoro-5-(trans-4-vinylcyclohexyl) benzene was dissolved in 100 ml of tetrahydrofuran, and then cooled to a temperature of −70° C. To the solution was then added dropwise 88 ml of a 1.53 mol/l n-hexane solution of n-butyllithium at a rate such that the liquid temperature was kept at −60° C. After 30 minutes of stirring, carbon dioxide was then introduced into the system at a rate such that the liquid temperature was kept at −60° C. When heat generation was terminated, the temperature of the reaction solution was returned to room temperature. To the reaction solution was then added 50 ml of a 10% hydrochloric acid. The reaction solution was then extracted with 250 ml of ethyl acetate. The resulting organic phase was washed with water and saturated brine, and then dried over anhydrous sodium sulfate. The solvents were then distilled off to obtain 28.9 g of 2,6-difluoro-4-(trans-4-vinylcyclohexyl)benzoic acid.

(b) Synthesis of 2,6-difluoro-4-(trans-4-vinylcyclohexyl) benzonitrile

To 20 g of 2,6-difluoro-4-(trans-4-vinylcyclohexyl) benzoic acid were then added 120 ml of 1,2-dichloroethane, 16 g of thionyl chloride and few drops of pyridine. The reaction mixture was then heated under reflux for 6 hours. The reaction mixture was then allowed to cool to room temperature. The solvents and excess thionyl chloride were distilled off under reduced pressure. To the residue was then added 150 ml of dichloromethane. The residue solution was then cooled to a temperature of 10° C. or lower. Ammonia was then introduced into the solution with stirring at a rate such that the liquid temperature was kept at 20° C. or lower. When heat generation was terminated, the solvents were then distilled off under reduced pressure. To the residue was then added 150 ml of N,N-dimethylformamide. The residue solution was then cooled to a temperature of 10° C. or lower. To the solution was then added dropwise 26.5 g of phosphorus oxychloride at a rate such that the liquid temperature was kept at 10° C. or lower. The temperature of the reaction solution was then returned to room temperature. The solution was then poured onto crushed ice. The resulting crystal was then filtered. The crystal thus obtained was washed with water, and then dried under reduced pressure. The crystal was then purified through silica gel column chromatography (solvent: toluene) to obtain 2,6-difluoro-4-(trans-4-vinylcyclohexyl)benzonitrile. The product was then recrystallized from ethanol to obtain 12.1 g of a purified product. The compound thus obtained had a melting point of 39° C.

Example 4

The compound of the general formula (Ia) obtained in Example 3 was used to prepare a nematic liquid crystal composition No. 3 which was then measured for various properties.

TABLE 3

Example 4

| | Host | | Comparative Example 4 (No. 3) | |
|---|---|---|---|---|
| Composition | 0d1CCPFf | 50% | 0d1CCPFf | 40% |
| | 0d3CCPFf | 50% | 0d3CCPFf | 40% |
| | | | (Ia) | 20% |
| $T_{N-I}$ (° C.) | 116.7 | | 82.0 | |
| T → N (° C.) | 11 | | 12 | |
| Vth (V) | 2.14 | | 1.26 | |
| Δε | 4.8 | | 8.3 | |
| Δn | 0.090 | | 0.091 | |

Example 5 and Comparative Example 3

A nematic liquid crystal composition No. 4 was prepared (Example 5), and then measured for various properties. For comparison, a composition falling outside the scope of the invention having almost the same $T_{N-I}$, threshold voltage and birefringence as that of Example 5 was prepared (Comparative Example 3). The composition ratio and ratio of properties of these compositions are set forth in Table 4 below. For the measurement of electro-optical properties in the table, STN-LCD was prepared under the condition of Δn·d=0.9.

Example 5 is excellent in temperature dependence of threshold voltage and steepness γ within the temperature of from −20° C. to 60° C. and shows a high contrast over a wide temperature range as compared with Comparative Example 3.

TABLE 4

Example 5 and Comparative Example 3

| | Example 5 (No. 4) | | Comparative Example 3 | |
|---|---|---|---|---|
| Composition | 2PEPCNff | 8% | 2PEPCNff | 2% |
| | 3PEPCNff | 5% | 3PEPCNff | — |
| | 4PEPCNff | 14% | 4PEPCNff | — |
| | 4PffEPCNf | — | 3PffEPCNf | 5% |
| | 5PffEPCNf | — | 5PffEPCNf | 5% |
| | 5PEPCNff | — | 5PEPCNff | 20% |
| | 0d1CPCNff | 15% | 0d1CPCNff | — |
| | 1d1CPCN | 5% | 1d1CPCN | 7% |
| | 1d3CPCN | — | 1d3CPCN | 7% |
| | 0d1CCPff | 21% | 0d1CCPff | 18% |
| | 0d3CCPff | — | 0d3CCPff | 6% |
| | 3CPtP2 | 4% | 3CPtP2 | 3% |
| | 4CPtP1 | 3% | 4CPtP1 | 3% |
| | 3CEPtP1 | 3% | 3CEPtP1 | 3% |
| | 3CEPtP5 | 3% | 3CEPtP5 | 3% |
| | 3CCPO(d3)1 | — | 3CCPO(d3)1 | 2% |
| | 4CCPO(d3)1 | — | 4CCPO(d3)1 | 2% |

TABLE 4-continued

Example 5 and Comparative Example 3

| | Example 5 (No. 4) | | | Comparative Example 3 | | |
|---|---|---|---|---|---|---|
| | 3CCEPC2 | 4% | | 3CCEPC2 | 4% | |
| | 3CCEPC3 | 5% | | 3CCEPC3 | 5% | |
| | 3CCEPC4 | 5% | | 3CCEPC4 | 5% | |
| | 3CCEPC5 | 4% | | 3CCEPC5 | — | |
| $T_{N-I}$ (° C.) | 97.2 | | | 101.2 | | |
| T → N (° C.) | −40 | | | −35 | | |
| Δn | 0.140 | | | 0.139 | | |
| η | 49.0 | | | 50.7 | | |
| STN properties | −20° C. | 25° C. | 60° C. | −20° C. | 25° C. | 60° C. |
| Vth | 1.420 | 1.200 | 1.179 | 1.412 | 1.193 | 1.160 |
| Vsat | 1.518 | 1.275 | 1.251 | 1.543 | 1.284 | 1.252 |
| γ | 1.069 | 1.063 | 1.051 | 1.093 | 1.076 | 1.079 |

Example 6 and Comparative Example 4

A nematic liquid crystal composition No. 5 was prepared (Example 6), and then measured for various properties. For comparison, a composition falling outside the scope of the invention having almost the same $T_{N-I}$, threshold voltage and birefringence as that of Example 5 was prepared (Comparative Example 4). The composition ratio and data of properties of these compositions are set forth in Table 5 below. For the measurement of electro-optical properties in the table, STN-LCD was prepared under the condition of Δn·d=0.9.

Example 6 is excellent in temperature dependence of threshold voltage and steepness γ within the temperature of from −20° C. to 25° C. and shows a high contrast over a wide temperature range as compared with Comparative Example 4. Example 4 was also observed to show reduced current flow as compared with Comparative Example 4.

TABLE 5

Example 6 and Comparative Example 4

| | Example 6 (No. 5) | | Comparative Example 4 | |
|---|---|---|---|---|
| Composition | 2PEPCNff | 5% | 2PEPCNff | 5% |
| | 3PEPCNff | 2% | 3PEPCNff | 2% |
| | 4PEPCNff | 3% | 4PEPCNff | 3% |
| | 5PEPCNff | — | 5PEPCNff | 15% |
| | 0d1CPCNff | 20% | 0d1CPCNff | — |
| | 1d1CPCN | 10% | 1d1CPCN | 10% |
| | 0d3CPCN | 10% | 0d3CPCN | 10% |
| | 3PtPO2 | — | 3PtPO2 | 3% |
| | 4PtPO2 | 5% | 4PtPO2 | 4.5% |
| | 5PtPO1 | 2% | 5PtPO1 | — |
| | 3CPO2 | — | 3CPO2 | 2.5% |
| | 3CPtP2 | 6% | 3CPtP2 | 5% |
| | 4CPtP1 | 5% | 4CPtP1 | 5% |
| | 3CEPtP1 | 6% | 3CEPtP1 | 5% |
| | 3CEPtP5 | 5% | 3CEPtP5 | — |
| | 0d1CCP1 | 4% | 0d1CCP1 | 15% |
| | 0d3CCP1 | 4% | 0d3CCP1 | 15% |
| | 3CCPO(d3)1 | 5% | 3CCPO(d3)1 | — |
| | 3CCEPC3 | 4% | 3CCEPC3 | — |
| | 3CCEPC4 | 4% | 3CCEPC4 | — |
| $T_{N-I}$ (° C.) | 93.3 | | 91.1 | |
| T → N (°0 C.) | −45 | | −47 | |
| Δn | 0.160 | | 0.160 | |
| η | 31.2 | | 30.3 | |
| STN properties | −20° C. | 25° C. | −20° C. | 25° C. |
| Vth | 1.54 | 1.43 | 1.53 | 1.37 |
| Vsat | 1.67 | 1.54 | 1.70 | 1.50 |
| γ | 1.084 | 1.076 | 1.118 | 1.094 |
| Ir ($\mu$A/cm$^2$) | — | 0.02 | | 0.06 |

Example 7 and Comparative Example 5

A nematic liquid crystal composition No. 6 was prepared (Example 7), and then measured for various properties. For comparison, a composition falling outside the scope of the invention having almost the same $T_{N-I}$, threshold voltage and birefringence as that of Example 5 was prepared (Comparative Example 5). The composition ratio and data of properties of these compositions are set forth in Table 6 below. For the measurement of electro-optical properties in the table, STN-LCD was prepared under the condition of $\Delta n \cdot d = 0.9$.

Example 7 is excellent in temperature dependence of threshold voltage within the temperature range of from 25° C. to 50° C. and steepness γ at 50° C. and shows a high contrast over a wide temperature range as compared with Comparative Example 5.

It was thus made obvious that the liquid crystal composition is excellent in all the systems of threshold voltage of 1.2 V 1.4 V and 2 V.

TABLE 6

Example 7 and Comparative Example 5

| | Example 7 (No. 6) | | | Comparative Example 5 | | |
|---|---|---|---|---|---|---|
| Composition | 0d1CPCNff | 10% | | 0d1CPCNff | — | |
| | 0d1CPCN | — | | 0d1CPCN | 7.2% | |
| | 1d1CPCN | 10% | | 1d1CPCN | 6.512% | |
| | 0d3CPCN | — | | 0d3CPCN | 4.04% | |
| | 4PmPCN | — | | 4PmPCN | 2% | |
| | 5PmPCN | — | | 5PmPCN | 2% | |
| | 3CPCN | — | | 3CPCN | 5.952% | |
| | 4CPCN | — | | 4CPCN | 1.6% | |
| | 5CPCN | — | | 5CPCN | 2% | |
| | 3PtP1 | — | | 3PtP1 | 3.304% | |
| | 4PtPO2 | 5% | | 4PtPO2 | — | |
| | 5PtPO1 | — | | 5PtPO1 | — | |
| | 0d3PZPOd3 | 15% | | 0d3PZPOd3 | 14% | |
| | 0d1CC5 | 20% | | 0d1CC5 | 20.792% | |
| | 0d3CC3 | 8% | | 0d3CC3 | 7.792% | |
| | 0d1CCPff | 10% | | 0d1CCPff | — | |
| | 3CPtP2 | 5% | | 3CPtP2 | 4.016% | |
| | 4CPtP1 | 5% | | 4CPtP1 | — | |
| | 3CEPtP1 | — | | 3CEPtP1 | 2.976% | |
| | 0d1CCP1 | 6% | | 0d1CCP1 | 7% | |
| | 0d3CCP1 | 6% | | 0d3CCP1 | 8.816% | |
| $T_{N-I}$ (° C.) | 87.8 | | | 86.4 | | |
| T → N (° C.) | −26 | | | −43 | | |
| Δn | 0.145 | | | 0.145 | | |
| η | 16.3 | | | 13.0 | | |
| STN properties | 25° C. | 50° C. | ΔV/ΔT | 25° C. | 50° C. | ΔV/ΔT |
| Vth | 2.35 | 2.23 | 4.8 mV | 2.32 | 2.08 | 9.6 mV |
| Vsat | 2.46 | 2.34 | | 2.41 | 2.21 | |
| γ | 1.046 | 1.050 | | 1.038 | 1.062 | |

Examples 8 and 9 Comparative Example 6

A nematic liquid crystal composition No. 7 was prepared (Example 8), and then measured for various properties. Further, a nematic liquid crystal composition No. 8 was prepared (Example 9), and then measured for various properties. The composition ratio and data of properties of these compositions are set forth in Table 7 below. For the measurement of electro-optical properties in the table, STN-LCD was prepared under the condition of $\Delta n \cdot d = 0.9$.

The comparison of the two compositions shows that Example 8 comprising 0d1CPCNff is excellent in temperature dependence of threshold voltage and steepness γ within the temperature of from −20° C. to 25° C. and shows an embodiment of about 20% in response at low temperatures as compared with Example 9 comprising 1d1CPCNff.

TABLE 7

Example 8 and Example 9

| | Example 8 (No. 7) | | Example 9 (No. 8) | |
|---|---|---|---|---|
| Composition | 2PEPCNff | 4% | 2PEPCNff | 4% |
| | 3PEPCNff | 3% | 3PEPCNff | 3% |
| | 4PEPCNff | 10% | 4PEPCNff | 10% |
| | 0d1CPCNff | 17% | 0d1CPCNff | — |
| | 1d1CPCNff | — | 1d1CPCNff | 17% |
| | 3CPCN | 3% | 3CPCN | 3% |
| | 0d1CC5 | 8% | 0d1CC5 | 8% |
| | 3CPO2 | 2% | 3CPO2 | 2% |
| | 4PtPO2 | 2% | 4PtPO2 | 2% |
| | 0d1CCPff | 9% | 0d1CCPff | 9% |
| | 3CPtP2 | 6% | 3CPtP2 | 6% |
| | 4CPtP1 | 6% | 4CPtP1 | 6% |
| | 3CEPtP1 | 6% | 3CEPtP1 | 6% |
| | 0d1CCP1 | 6% | 0d1CCP1 | 6% |
| | 0d3CCP1 | 14% | 0d3CCP1 | 14% |
| | 3CCEPC3 | 2% | 3CCEPC3 | 2% |
| | 3CCEPC4 | 2% | 3CCEPC4 | 2% |
| $T_{N-I}$ (° C.) | 87.6 | | 90.3 | |
| T → N (° C.) | −49 | | −45 | |
| Δn | 0.135 | | 0.137 | |
| η | 25.6 | | 26.6 | |
| STN properties | −20° C. | 25° C. | −20° C. | 25° C. |
| Vth | 1.483 | 1.471 | 1.498 | 1.480 |
| Vsat | 1.560 | 1.551 | 1.591 | 1.560 |
| γ | 1.052 | 1.054 | 1.062 | 1.054 |
| τ | 2.909 | 173 | 3.465 | 178 |

A composition falling outside the invention comprising 2CPCNff instead of 0d1CPCNff of Example 8 was prepared (Comparative Example 6). The composition ratio and data of properties of Comparative Example 6 are set forth in Table 8 together with that of Example 8. For the measurement of electro-optical properties in the table, STN-LCD was prepared under the condition of $\Delta n \cdot d = 0.9$.

The comparison of the two compositions shows that Example 8 comprising 0d1CPCNff is excellent in temperature dependence of threshold voltage and steepness γ within the temperature of from −20° C. to 25° C. and shows an enhancement of about 23% in response at low temperatures as compared with Comparative Example 6 comprising 2CPCNff.

TABLE 8

Example 8 and Comparative Example 6

| | Example 8 (No. 7) | | Comparative Example 6 | |
|---|---|---|---|---|
| Composition | 2PEPCNff | 4% | 2PEPCNff | 4% |
| | 3PEPCNff | 3% | 3PEPCNff | 3% |
| | 4PEPCNff | 10% | 4PEPCNff | 10% |
| | 0d1CPCNff | 17% | 0d1CPCNff | — |
| | 2CPCNff | — | 2CPCNff | 17% |
| | 3CPCN | 3% | 3CPCN | 3% |
| | 0d1CC5 | 8% | 0d1CC5 | 8% |
| | 3CPO2 | 2% | 3CPO2 | 2% |
| | 4PtPO2 | 2% | 4PtPO2 | 2% |
| | 0d1CCPff | 9% | 0d1CCPff | 9% |
| | 3CPtP2 | 6% | 3CPtP2 | 6% |
| | 4CPtP1 | 6% | 4CPtP1 | 6% |
| | 3CEPtP1 | 6% | 3CEPtP1 | 6% |
| | 0d1CCP1 | 6% | 0d1CCP1 | 6% |
| | 0d3CCP1 | 14% | 0d3CCP1 | 4% |
| | 3CCEPC3 | 2% | 3CCEPC3 | 2% |
| | 3CCEPC4 | 2% | 3CCEPC4 | 2% |
| $T_{N-I}$ (° C.) | 87.6 | | 88.0 | |
| T → N (° C.) | −49 | | −40 | |
| Δn | 0.135 | | 0.136 | |
| η | 25.6 | | 27.5 | |

TABLE 8-continued

Example 8 and Comparative Example 6

|  | Example 8 (No. 7) |  | Comparative Example 6 |  |
|---|---|---|---|---|
|  | −20° C. | 25° C. | −20° C. | 25° C. |
| STN properties |  |  |  |  |
| Vth | 1.483 | 1.471 | 1.492 | 1.460 |
| Vsat | 1.560 | 1.551 | 1.598 | 1.553 |
| γ | 1.052 | 1.054 | 1.071 | 1.064 |
| τ | 2.909 | 173 | 3.534 | 178 |

The combination of liquid crystal materials of the invention makes it possible to obtain a liquid crystal composition which shows reduced current flow and exhibits a high dielectric anisotropy. When used as a liquid crystal display device, the liquid crystal composition of the invention exhibits a high contract and reliability and thus is excellent. This liquid crystal display is very useful as STN-LCD or TN-LCD.

While the invention has been described in detail and with reference to specific embodiments thereof, it will be apparent to one skilled in the art that various changes and modifications can be made therein without departing from the spirit and scope thereof.

This application is based on Japanese patent application No. Hei-11-306820 filed on Oct. 28, 1999, the entire contents of which incorporated herein by reference.

What is claimed is:

1. A liquid crystal composition comprising as a first liquid crystal component at least one compound selected from the group consisting of compounds represented by the following general formula (I):

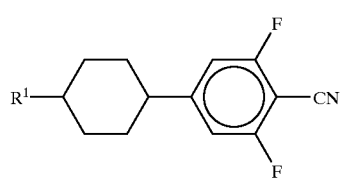

wherein $R^1$ represents a $C_{2-16}$ alkenyl group or a $C_{3-16}$ alkenyloxy group
and as a second liquid crystal component at least one compound selected from the group consisting of compounds represented by the following general formulae (II) and (III):

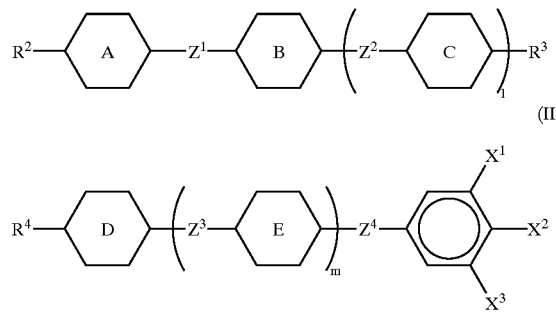

wherein $R^2$, $R^3$ and $R^4$ each independently represents a $C_{1-16}$ alkyl or alkoxy group which may be substituted by a fluorine atom, a $C_{2-16}$ alkenyl group which may be substituted by a fluorine atom, a $C_{3-16}$ alkenyloxy group which may be substituted by a fluorine atom or a $C_{1-10}$ alkoxyl group-substituted $C_{1-12}$ alkyl group which may be substituted by a fluorine atom; the rings A, B, C, D and E each independently represents a 1,4-phenylene group, 2-methyl-1,4-phenylene group, 3-methyl-1,4-phenylene group, naphthalene-2,6-diyl group, phenanthrene-2,7-diyl group, fluorene-2,7-diyl group, trans-1,4-cyclohexylene group, 1,2,3,4-tetrahydronaphthalene-2,6-diyl group, decahydronaphthalene-2,6-diyl group, trans-1,3-dioxane-2,5-diyl group, pyridine-2,5-diyl group, pyrimidine-2,5-diyl group, pyrazine-2,5-diyl group or pyridazine-2,5-diyl group, each of which may be substituted by a fluorine atom; l and m each independently represents 0, 1 or 2; $Z^1$, $Z^2$, $Z^3$ and $Z^4$ each independently represents a single bond, —CH$_2$CH$_2$—, —(CH$_2$)$_4$—, —OCH$_2$—, —CH$_2$O—, —CH=CH—, —CH=N—N=CH— or —C≡C—; $X^2$ represents a cyano group, a fluorine atom, a chlorine atom, a trifluoromethoxy group, a trifluoromethyl group, a difluoromethoxy group, a hydroxy atom, a 3,3,3-trifluoroethoxy group, R' or —OR' in which R' represents a $C_{1-12}$ straight-chain alkyl group or a $C_{2-12}$ straight-chain alkenyl group; and $X^1$ and $X^3$ each independently representss a hydrogen atom, a fluorine atom or a chlorine atom, with the proviso that when $R^4$ is an alkenyl or alkenyloxy group, $X^2$ is a cyano group, the ring D is a trans-1,4-cyclohexylene group, m is 0, and $Z^4$ is a single bond, $X^1$ and $X^3$ are not a fluorine atom at the same time and said composition having a nematic phase upper temperature limit of 75° C. or higher and a birefringence (Δn) of from 0.07 to 0.24.

2. The liquid crystal composition according to claim 1, wherein the content of the at least one compound of the general formula (I) in the composition is from 5 to 40% by weight and the content of the at least one compound selected from the group consisting of compounds represented by the formulae (II) and (III) in the composition is from 5 to 95% by weight.

3. The liquid crystal composition according to claim 1, wherein as the compound of the general formula (II) there is incorporated at least one compound selected from the group consisting of compounds of the following general formula (II-a):

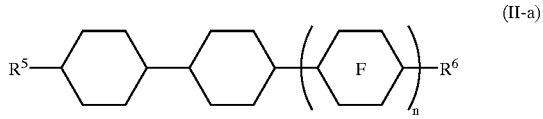

wherein $R^5$ and $R^6$ have the same meaning as $R^2$ and $R^3$, respectively; the ring F represents a 1,4-phenylene group or trans-1,4-cyclohexylene group; and n represents 0 or 1.

4. The liquid crystal composition according to claim 3, wherein the content of the at least one compound of the general formula (I) in the composition is from 5 to 40% by weight and the content of the at least one compound of the general formula (II-a) in the composition is from 5 to 95% by weight.

5. The liquid crystal composition according to claim 1, wherein as the compound of the general formula (III) there is incorporated at least one compound selected from the group consisting of compounds of the following general formula (III-a):

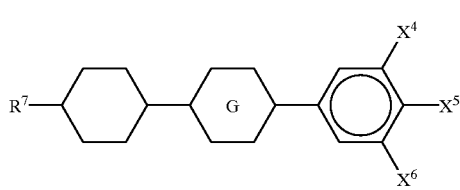

(III-a)

wherein $R^7$ represents a $C_{1-8}$ alkyl group or a $C_{2-8}$ alkenyl group; the ring G represents a 1,4-phenylene group or a trans-1,4-cyclohexylene group; $X^5$ represents a cyano group, a fluorine atom, a trifluoromethoxy group or a difluoromethoxy group; and $X^4$ and $X^6$ each independently represents a hydrogen atom or a fluorine atom.

6. The liquid crystal composition according to claim 5, wherein the content of the at least one compound of the general formula (I) in the composition is from 5 to 40% by weight and the content of the at least one compound of the general formula (III-a) in the composition is from 5 to 95% by weight.

7. The liquid crystal composition according to claim 1, wherein said composition comprises as the first liquid crystal component at least one compound of the general formula (I) in an amount of from 5 to 40% by weight, and as the second liquid crystal component at least one compound selected from the group consisting of compounds represented by the following general formula (II-b) in an amount of from 5 to 40% by weight:

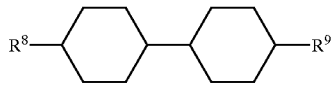

(II-b)

wherein $R^8$ and $R^9$ each independently represents a $C_{1-8}$ alkyl group or a $C_{2-8}$ alkenyl group and at least one compound selected from the group consisting of compounds represented by the following general formula (II-c) in an amount of from 5 to 60% by weight:

(II-c)

wherein $R^{10}$ and $R^{11}$ each independently represents a $C_{1-8}$ alkyl group or a $C_{2-8}$ alkenyl group.

8. The liquid crystal composition according to claim 1, wherein said composition comprises as the first liquid crystal component at least one compound of the general formula (I) in an amount of from 5 to 40% by weight and as the second liquid crystal component at least one compound selected from the group consisting of compounds represented by the following general formula (III-a) in an amount of from 5 to 40% by weight:

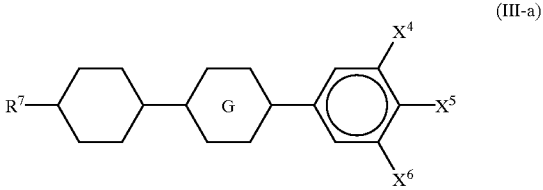

(III-a)

wherein $R^7$ represents a $C_{1-8}$ alkyl group or a $C_{2-8}$ alkenyl group; the ring G represents a 1,4-phenylene group or a trans-1,4-cyclohexylene group; $X^5$ represents a cyano group, a fluorine atom, a trifluoromethoxy group or a difluoromethoxy group; and $X^4$ and $X^6$ each independently represents a hydrogen atom or a fluorine atom, and at least one compound selected from the group consisting of compounds represented by the following general formula (II-b) and (II-c) in an amount of from 5 to 60% by weight:

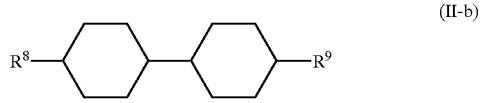

(II-b)

wherein $R^8$ and $R^9$ each independently representss a $C_{1-8}$ alkyl group or a $C_{2-8}$ alkenyl group,

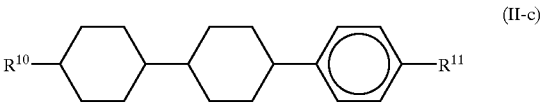

(II-c)

wherein $R^{10}$ and $R^{11}$ each independently representss a $C_{1-8}$ alkyl group or a $C_{2-8}$ alkenyl group.

9. The liquid crystal composition according to claim 1, wherein in said composition comprises as the first liquid crystal component at least one compound of the general formula (I) in an amount of from 5 to 40% by weight and as the second liquid crystal component at least one compound selected from the group consisting of compounds represented by the following general formula (III-a) in an amount of from 5 to 40% by weight:

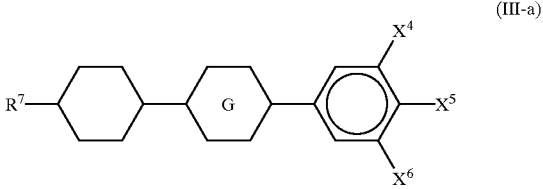

(III-a)

wherein $R^7$ represents a $C_{1-8}$ alkyl group or a $C_{2-8}$ alkenyl group; the ring G represents a 1,4-phenylene group of a trans-1,4-cyclohexylene group; $X^5$ represents a cyano group, a fluorine atom, a trifluoromethoxy group or a difluoromethoxy group; and $X^4$ and $X^6$ each independently representss a hydrogen atom or a fluorine atom, at least one compound selected from the group consisting of compounds represented by the following general formula (II-b) in an amount of from 5 to 40% by weight:

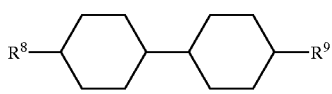
(II-b)

wherein $R^8$ and $R^9$ each independently representss a $C_{1-8}$ alkyl group or a $C_{2-8}$ alkenyl group, and at least one compound selected from the group consisting of compounds represented by the following general formula (II-c) in an amount of from 5 to 40% by weight:

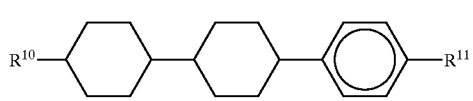
(II-c)

wherein $R^{10}$ and $R^{11}$ each independently represents a $C_{1-8}$ alkyl group or a $C_{2-8}$ alkenyl group.

10. The liquid crystal composition according to claim 1, wherein as the compound of the general formula (III) there is incorporated at least one compound selected from the group consisting of compounds represented by the following general formula (III-b):

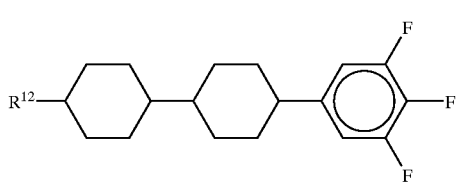
(III-b)

wherein $R^{12}$ represents a $C_{1-16}$ alkyl group or a $C_{2-8}$ alkenyl group in an amount of from 5 to 40% by weight.

11. The liquid crystal composition according to claim 1, wherein as the compound of the general formula (III) there is incorporated at least one compound selected from the group consisting of compounds represented by the following general formula (III-c):

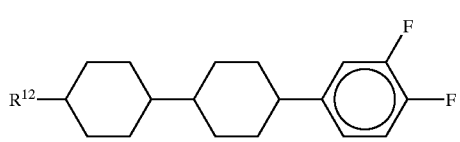
(III-c)

wherein $R^{12}$ represents a $C_{1-16}$ alkyl group or a $C_{2-8}$ alkenyl group in an amount of from 5 to 40% by weight.

12. The liquid crystal composition according to claim 1, wherein as said first component there is incorporated a compound represented by the general formula (Ia)

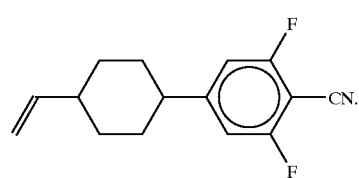
(Ia)

13. A liquid crystal composition comprises as the first liquid crystal component a compound represented by the general formula (I):

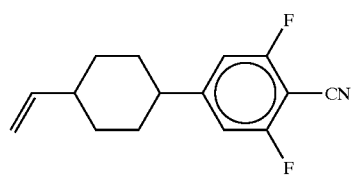
(Ia)

and as the second liquid crystal component at least one compound represented by the following general formula (III-a) in an amount of from 5 to 40% by weight:

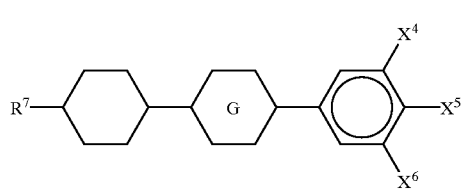
(III-a)

wherein $R^7$ represents a $C_{1-8}$ alkyl group or a $C_{2-8}$ alkenyl group; the ring G represents a 1,4-phenylene group or a trans-1,4-cyclohexylene group; $X^5$ represents a cyano group, a fluorine atom, a trifluoromethoxy group or a difluoromethoxy group; and $X^4$ and $X^6$ each independently represents a hydrogen atom or a fluorine atom and at least one compound selected from the group consisting of compounds represented by the following general formulae (II-b) and (II-c) in an amount of from 5 to 60% by weight:

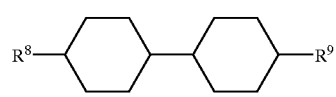
(II-b)

wherein $R^8$ and $R^9$ each independently representss a $C_{1-8}$ alkyl group or a $C_{2-8}$ alkenyl group:

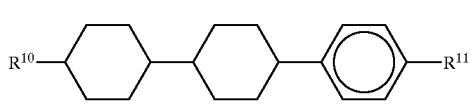
(II-c)

wherein $R^{10}$ and $R^{11}$ each independently representss a $C_{1-8}$ alkyl group or a $C_{2-8}$ alkenyl group.

14. The nematic liquid crystal composition according to claim 1, which satisfies at least one of the following requirements:
(i) $0.11 \leq \Delta n \leq 0.195$;
(ii) $4 \leq \Delta\epsilon \leq 60$;
(iii) $1.1 \leq K33/K11 \leq 3$;
(iv) $10 \text{ m.Pas} \leq \eta \leq 80 \text{ m.Pas}$; and
(v) $75° \text{ C.} \leq T_{N-I} \leq 130° \text{ C.}$ wherein the measurement for the requirements (i) to (iv) are made at 20° C., $\Delta n$ represents a birefringence, $\Delta\epsilon$ represents a dielectric anisotropy, K33/K11 represents an elastic constant ratio, K33 represents a bend elastic constant, K11 represents a splay elastic constant, $\eta$ represents a viscosity and $T_{N-I}$ represents nematic phase-isotropic liquid phase transition temperature.

15. The nematic liquid crystal composition according to claim 13, which satisfies at least one of the following requirements:

(i) $0.11 \leq \Delta n \leq 0.195$;

(ii) $4 \leq \Delta \epsilon \leq 60$;

(iii) $1.1 \leq K33/K11 \leq 3$;

(iv) $10 \text{ m.Pas} \leq \eta \leq 80 \text{ m.Pas}$; and (v) $75° \text{ C.} \leq T_{N-I} \leq 130° \text{ C.}$ wherein the measurement for the requirements (i) to (iv) are made at 20° C., $\Delta n$ represents a birefringence, $\Delta \epsilon$ represents a dielectric anisotropy, K33/K11 represents an elastic constant ratio, K33 represents a bend elastic constant, K11 represents a splay elastic constant, $\eta$ represents a viscosity and $T_{N-I}$ represents nematic phase-isotropic liquid phase transition temperature.

16. A liquid crystal display device comprising the liquid crystal composition according to claim 1.

17. A super-twisted nematic (STN) liquid crystal display device comprising the liquid crystal composition according to claim 1, having a twist angle of from 220° to 270° and satisfying at least one of the following requirements (i) to (iii) when the driving temperature falls within the range of from −20° C. to 60° C.:

(i) $\Delta V/\Delta T$ (temperature dependence of Vth)$\leq 7$ mV/° C.;

(ii) steepness $\gamma$ (ratio of saturation voltage to threshold voltage (Vth))$\leq 1.15$; and (iii) ratio of minimum to maximum of steepness $\gamma$ in the foregoing temperature range$\leq 3\%$.

18. A super-twisted nematic (STN) liquid crystal display device comprising the liquid crystal composition according to claim 13, having a twist angle of from 220° to 270° and satisfying at least one of the following requirements (i) to (iii) when the driving temperature falls within the range of from −20° C. to 60° C.:

(i) $\Delta V/\Delta T$ (temperature dependence of Vth)$\leq 7$ mV/° C.;

(ii) steepness $\gamma$ (ratio of saturation voltage to threshold voltage (Vth))$\leq 1.15$; and (iii) ratio of minimum to maximum of steepness $\gamma$ in the foregoing temperature range$\leq 3\%$.

* * * * *